United States Patent [19]

McKinnon et al.

[11] Patent Number: 5,064,413
[45] Date of Patent: Nov. 12, 1991

[54] NEEDLELESS HYPODERMIC INJECTION DEVICE

[75] Inventors: Charles M. McKinnon, Laguna Niguel; Takaaki Nakagawa, Costa Mesa, both of Calif.; Carl E. Wilcox, Portland, Oreg.

[73] Assignee: Bioject, Inc., Portland, Oreg.

[21] Appl. No.: 434,250

[22] Filed: Nov. 9, 1989

[51] Int. Cl.⁵ .............................................. A61M 5/30
[52] U.S. Cl. ....................................... 604/70; 604/72; 604/143
[58] Field of Search ..................... 604/68–72, 604/140, 141, 143, 228, 232; 222/389

[56] References Cited

U.S. PATENT DOCUMENTS

| | | | |
|---|---|---|---|
| 2,025,219 | 12/1935 | Smith | 604/232 X |
| 2,547,099 | 4/1951 | Smoot . | |
| 2,605,763 | 8/1952 | Smoot . | |
| 2,653,602 | 9/1953 | Smooth . | |
| 2,704,543 | 3/1955 | Scherer . | |
| 2,737,946 | 3/1956 | Hein, Jr. . | |
| 2,764,977 | 10/1956 | Ferguson . | |
| 3,110,309 | 11/1963 | Higgins | 604/232 X |
| 3,292,621 | 7/1963 | Banker . | |
| 3,292,622 | 12/1966 | Banker . | |
| 3,515,130 | 6/1970 | Tsujino . | |
| 3,561,443 | 2/1971 | Banker . | |
| 3,688,765 | 9/1972 | Gasaway . | |
| 3,945,379 | 3/1976 | Pritz et al. | 604/70 |
| 4,059,107 | 11/1977 | Iriguchi . | |
| 4,124,024 | 11/1978 | Schwebel . | |
| 4,421,508 | 12/1983 | Cohen | 604/70 |
| 4,507,113 | 3/1985 | Dunlap . | |
| 4,596,556 | 6/1986 | Morrow . | |
| 4,626,242 | 12/1986 | Fejes et al. | 604/68 |
| 4,634,027 | 1/1987 | Kanarvogel | 222/380 |
| 4,680,027 | 7/1987 | Parsons et al. | 604/68 |
| 4,790,824 | 12/1988 | Morrow et al. | 604/143 |
| 4,874,367 | 10/1989 | Edwards . | |

FOREIGN PATENT DOCUMENTS 8703494 6/1987 PCT Int'l Appl. .

Primary Examiner—John D. Yasko
Assistant Examiner—Adam J. Cermak
Attorney, Agent, or Firm—Lyon & Lyon

[57] ABSTRACT

A needleless injection device has a housing containing a pilot valve connectable to a compressed gas source. A main valve is operatively connected to the pilot valve. The pilot valve and main valve form a two-stage valve with the pilot valve activatable to open the main valve utilizing gas pressure. Compressed gas in a reservoir flows through the open main valve to driven a plunger into an ampule to inject an injectant through a patient's skin.

30 Claims, 4 Drawing Sheets

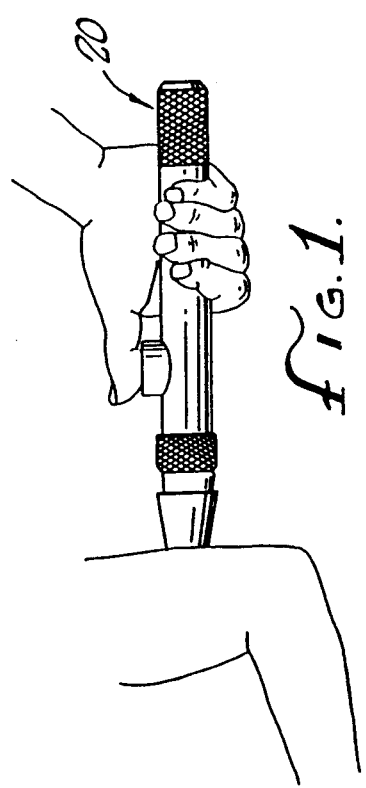
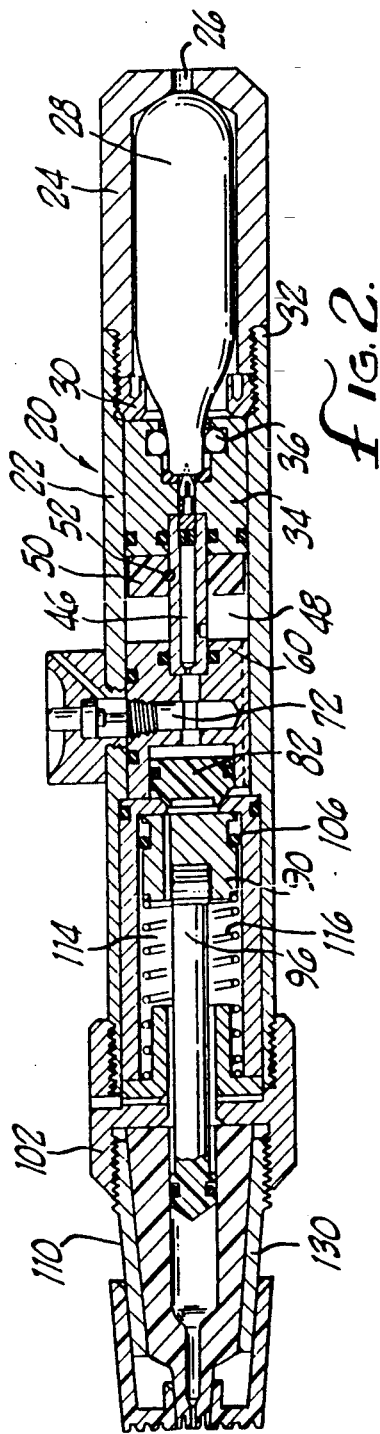
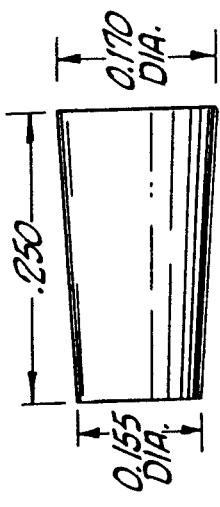

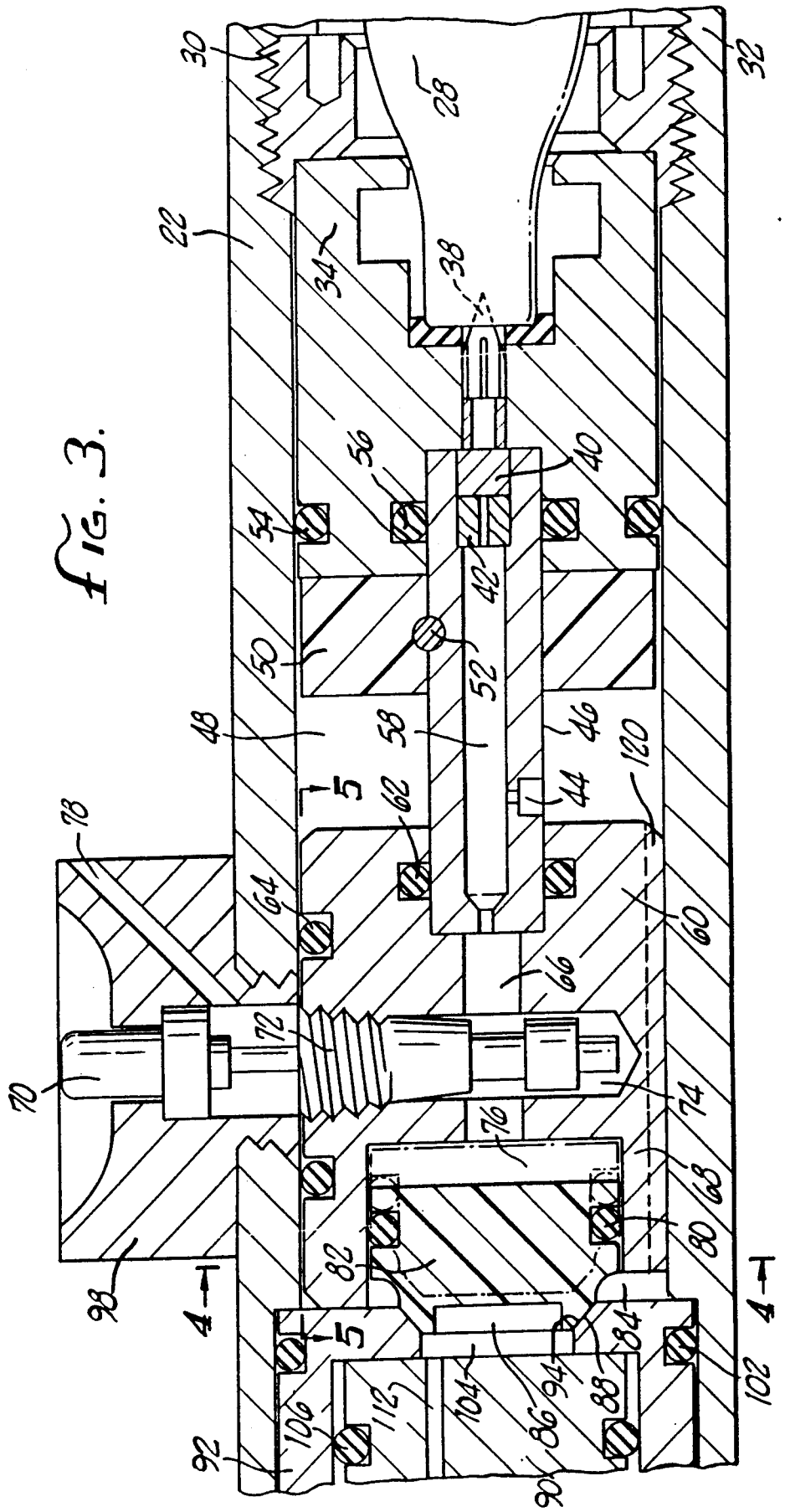

NEEDLELESS HYPODERMIC INJECTION DEVICE

BACKGROUND OF THE INVENTION

The field of the present invention is needleless hypodermic injection devices. More particularly, the invention relates to needleless hypodermic devices utilizing pressurized gas for injection of medication.

Various needleless hypodermic injection devices have been known in the past. For example, Morrow et al, U.S. Pat. No. 4,790,824 describes a needleless hypodermic injection device having a two-stage gas delivery system and an ampule shroud containing medication which is driven through the skin via gas pressure.

Parsons et al, U.S. Pat. No. 4,680,027 discloses an injection device using a pressurized gas cartridge to drive a piston against the biasing force of a spring. The driven piston works on a syringe causing liquid medication to be ejected with sufficient pressure to penetrate the skin of the patient.

While these and other known injection devices have met with varying degrees of success, their constructions or operating features can prevent effective injection. It has now been discovered that the injection of liquid medication should be as instantaneous as possible. With gas powered injection devices, the rise time of the gas pressure acting on the syringe, and the resulting acceleration at which the syringe is driven, is critical. When the gas pressure acting on the syringe rises too slowly, the initial medication ejected from the syringe does not have sufficient pressure or velocity to pass through the skin. In addition, if the "rise time" of the injection sequence is not sufficiently fast, a substantial portion of the medication will be too slowly driven from the syringe causing a "splash back" condition. Consequently, as a result of "splash back" the patient does not receive the full dosage of medication.

In gas driven injection devices, there are several factors which may affect the efficiency of the device. For example, devices having a long or tortuous gas path will have slower rise times due to flow losses and gas volume compressibility effects. In addition, certain injection devices rely on direct mechanical valve operation by the user of the device to release the gas pressure during the injection sequence. Since the valve operation is done manually in these devices, the effectiveness of the injection can vary widely with the user, due to the speed, activating force and completeness of activating movement employed by different users of the device. More importantly, it has not been previously appreciated that many of these types of devices have relatively large "dead" spaces or volumes of gas trapped behind the piston when the device in the ready to fire condition. These dead volumes substantially hinder injection by slowing the rise time of the gas pressure acting on the piston since substantial time is required for relatively large volumes of gas to flow into the dead volumes to build up an adequate injection pressure.

Accordingly, it is an object of the invention to provide an improved needleless hypodermic injection device.

It is another object of the invention to provide a novel ampule assembly which may be advantageously used with such a needleless injection device.

It is another object of the invention to provide a novel method of subcutaneous or intramuscular injection.

SUMMARY OF THE INVENTION

These and other related objects are achieved according to the invention by an injection device having a piercing body within a housing and a valve body in the housing spaced apart from the piercing body. A gas delivery tube extends from the piercing body to the valve body. A reservoir is formed by the valve body and the housing, and the gas delivery tube has a bleed hole opening into the reservoir. A pilot valve is substantially disposed in a pilot valve chamber in the valve body and a main valve piston is slidably positioned within the housing. A liner having a liner seat with the main valve piston sealingly engages against the liner seat. The main valve piston faces an annular chamber on one side with the annular chamber connected to the reservoir via a gas passageway. A main valve piston chamber is on the other side of the main valve piston and is connected to the pilot valve chamber. The pilot valve is activatable to vent the pilot valve chamber. This causes the main valve piston to separate from the liner seat such that compressed gas from the reservoir flows past the main valve piston into a plunger chamber to rapidly drive a plunger into a medication ampule for needleless injection through the skin.

BRIEF DESCRIPTION OF THE DRAWINGS

Other objects and features of the present invention will become apparent from the following detailed description taken in connection with the accompanying drawings. It is to be understood, however, that the drawings are designed for the purpose of illustration only and are not intended as a definition of the limits of the invention.

In the drawings wherein similar reference characters denote similar elements throughout the several views:

FIG. 1 is a perspective view of the present needleless injection device in the ready for injection state;

FIG. 2 is a side view in part section of the injection device of FIG. 1;

FIG. 3 is an enlarged fragment view in part section of the valve mechanisms and gas delivery system of the device of FIG. 2;

FIG. 6 is a side view of the Luer fitting provided on the ampule shown in FIGS. 2 and 7.

DETAILED DESCRIPTION OF THE PREFERRED EMBODIMENTS

Figure 4:
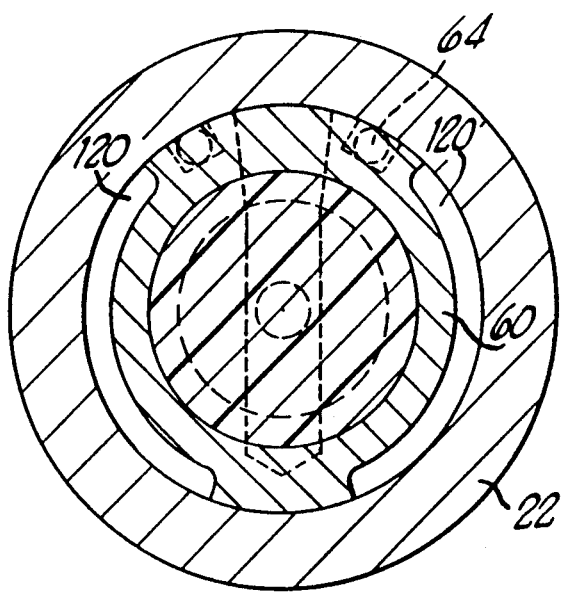
FIG. 4 is an enlarged section view taken along line 4—4 of FIG. 3.
Figure 5:
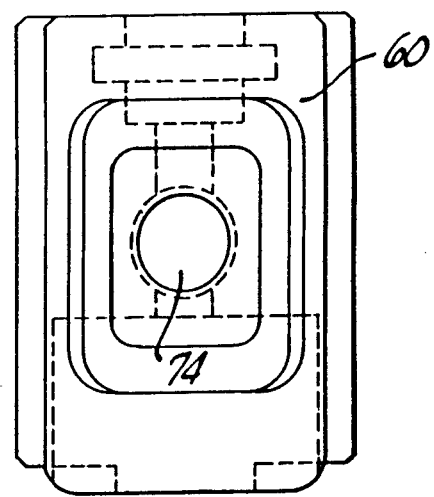
FIG. 5 is a top interior view taken along line 5—5 of FIG. 4.

Referring now in detail to the drawings, therein illustrated is a novel needleless hypodermic injection device, which as shown in FIGS. 1 and 2 includes a housing 22 and a cartridge holder 24 threaded onto an internal threaded section 32 of the housing 22 and holding a cartridge 28. At room temperature, the cartridge 28 contains a saturated gas/liquid, such as $CO_2$ or some other appropriate pressure medium, hereinafter referred to as "compressed gas". An opening 26 is provided in the cartridge holder 24. A spanner collar 30 is threaded onto the internal threaded section 32 of the housing 22 ahead of the cartridge holder 24 and serves to hold other internal components in place.

Turning to FIG. 3, a piercing body 34 is contained within the housing 22 against the spanner collar 30. An elastomeric washer 36 within the piercing body seals against the facing end of the cartridge 28. A piercing pin 38 extends outwardly from the piercing body 34 into the cartridge 28. The piercing pin 38 connects to a gas delivery tube 46. A filter 40 and an orifice 42 are secured within the gas delivery tube 46.

Spaced apart from the piercing body 34 within the housing 22 is a valve body 60. The valve body 60, housing 22, and piercing body 34 form a reservoir 48 around the gas delivery tube 46. A bleed hole 44 leads from the gas delivery tube to the reservoir 48. A spacer 50 is optionally secured around the gas delivery tube 46 within the reservoir 48 by a pin 52.

An O-ring 54 seals the piercing body against the inner surface of the housing 22. Similarly, an O-ring 56 seals the gas delivery tube 46 to the piercing body 34.

At the other end of the gas delivery tube 46, an O-ring 62 seals the gas delivery tube 46 to the valve body 60, with the gas delivery tube extending into a bore 66 running through the valve body 60. A pilot valve 72, preferably a Schrader-type poppet valve, is contained within a pilot valve chamber 74 within the valve body 60. The valve body 60 includes a sleeve section 68 substantially containing a main valve piston 82. An O-ring 80 seals the main valve piston 82 against the inner surfaces of the sleeve section 68 of the valve body 60 with the main valve piston 82 slidably disposed therein. In between the main valve piston 82 and the pilot valve chamber 74 is a main piston chamber 76, with the bore 66 also extending from the pilot valve chamber 74 to the main piston chamber 76. As shown in FIG. 4, gas passageways 120 extend along the periphery of the valve body 60 to connect the reservoir 48 to an annular chamber 84. The gas passageways 120 are designed to maximize unrestricted flow from the reservoir 48 into the plunger chamber 114.

The main valve piston 82 includes a piston face 88 for sealing against a valve or liner seat 94 of a liner 92. Alternatively, the seat may be formed on an inwardly extending annular rim section of the housing 22. The main valve piston 82 and liner seat 94 form the main valve of the injection device. The main valve piston 82 is advantageously made of TEFLON and also preferably has a counter bore 86 for improved sealing characteristics.

A button 70 is held against the pilot valve 72 within a button housing 98. An O-ring 64 seals the valve body 60 to the inner surface of the housing 22, around the pilot valve 72 which passes partially through the housing 22. A vent 78 extends through the button housing 98 into the pilot valve chamber 74.

The liner 92 has an opening 104 adjacent the liner seat 94 and is sealed against the inner surface of the housing 22 by O-ring 102. The sleeve section 68, the liner 92 and the main valve piston 82 form a seat chamber or annular chamber 84 on the side of the main valve piston 82 opposite of the main piston chamber 76.

Within the liner 92 is a plunger driver 90 engaging a plunger 96. A plunger driver orifice 112 extends through the plunger driver 90 connecting the liner opening 104 to the plunger chamber 114. As shown in FIG. 2, a compression spring 116 is positioned on a hub 1!8 extending into the plunger chamber 114. The spring 116 biases the plunger driver 90 against the end of the liner 92 adjacent the liner seat 94. An O-ring 106 seals the plunger driver 90 against the liner 92.

Figure 7:
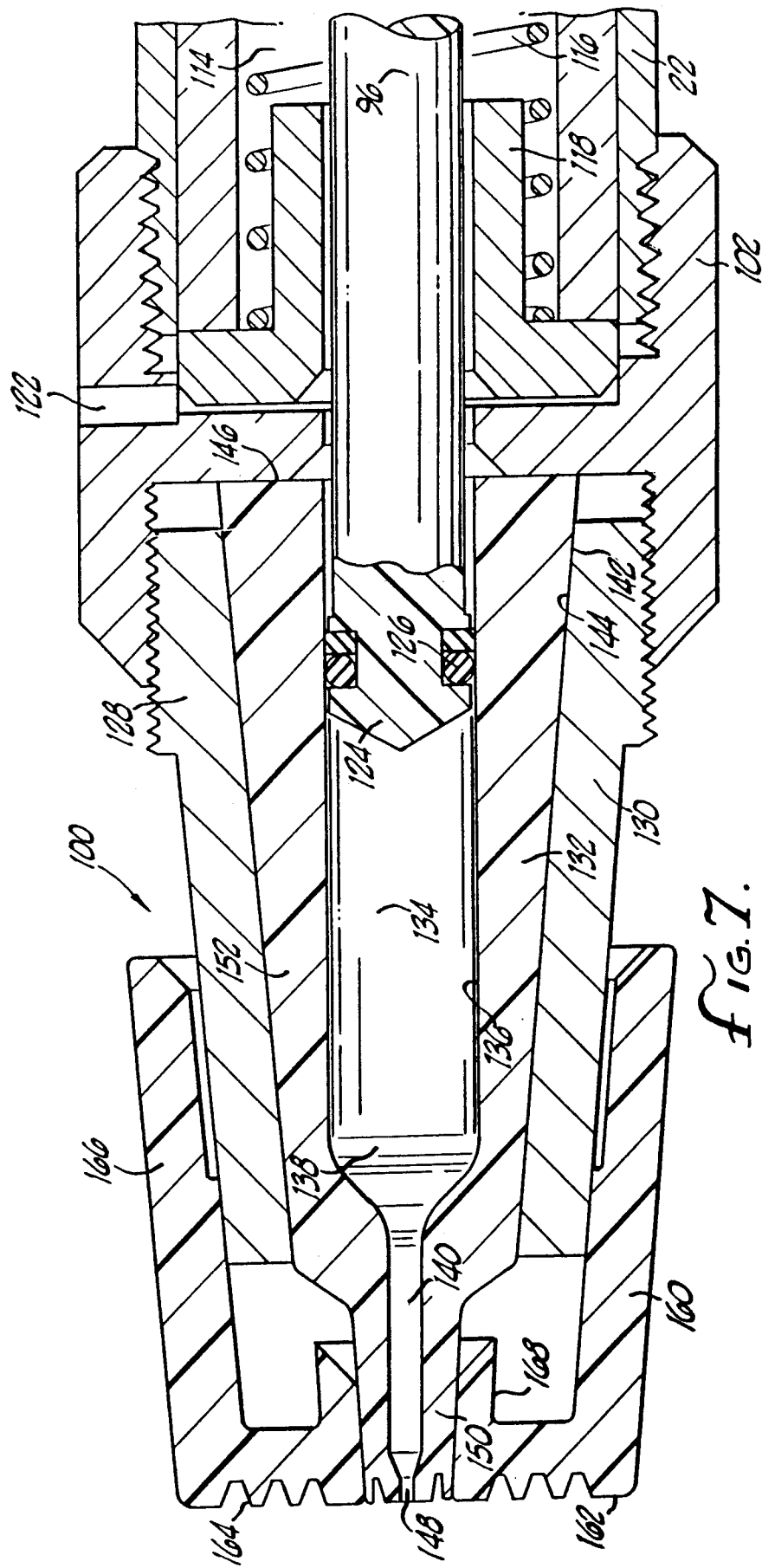
FIG. 7 is an enlarged section view fragment of an ampule which may be used with the injection device.

Referring now to FIG. 7, a threaded collar 102 having a vent 122 leading to the plunger chamber 114 joins the housing 22 and a threaded end 128 of an ampule holder 130. Within the ampule holder 130 is an ampule 132 having a base 146 abutting the threaded collar 102. The conically tapered inner surface of the ampule holder 144 matches the conically tapered outer surface 142 of the ampule 132, to support the ampule walls 152 all around. With shallow angles of taper, there is a tendency for the ampule 132 to stick in the ampule holder 130 after the injunction. This is called a locking taper. The ampule 132 and ampule holder 130 preferably have approximately a 16 degree taper which is advantageously above the locking taper range. The ampule 132 is advantageously a single molded piece. A breech lock fitting may alternately be provided for quick ampule replacement.

The plunger 96 has a tapered end 124 and a seal 126 extending into an injectant chamber 134 within the ampule 130. The plunger seal 126 seals the plunger 124 against the injectant chamber walls 136, which are substantially parallel. The injectant chamber 134 leads to a flow path comprising a first transition 138 extending into a throat !40 leading to a second transition 149 and a nozzle 148. The flow path smoothly makes the cross section area reduction from the injectant chamber 134 to the nozzle 148, to minimize flow losses. Around the outside of the nozzle end of the throat 140 of the ampule 132 is an ANSI standard Luer fitting 150 as detailed in FIG. 6. This fitting permits connection of the ampule 132 to another medical device or container in a leak proof and mechanically secure manner. Advantageously, an ampule 132 made of or lined with glass or another material which does not interact with the desired injectant may be used. The injectant chamber 134, first transition 138, throat 140, second transition 149 and nozzle 148 are preferably molded in as part of the ampule during its manufacture.

A shield 160 is preferably provided over the ampule 132 and at least part of the ampule holder 130. The shield 160 includes a Luer sleeve 168 adapted to fit over the Luer fitting 150 of the ampule 132. The front surface 162 of the shield 160 has ridges 164. A cylindrical flange 166 extends back from the front surface 162 and engages the ampule holder 130.

In operation, the cartridge holder 24 is unscrewed from the housing 22 of the injection device 20. A compressed gas cartridge 28, such as a $CO_2$ cartridge is placed into the cartridge holder 24. The cartridge holder 24 is then threaded back onto the internal threaded section 32 of the housing 22. As the cartridge holder 24 is turned to engage the housing 22, the face end of the neck of the cartridge 24 engages, compresses and seals against the elastomeric washer 36 and the cartridge 28 is pierced by the piercing pin 3 projecting from the piercing body 34. After the cartridge 28 is pierced, compressed gas flows by the piercing pin 38, through the filter 40 and the orifice 42. The filter 40 traps any contaminants in the gas flow. The orifice 42 limits the flow rate.

Compressed gas flows through the orifice 42 and fills the duct 58 within the gas delivery tube 46. The gas continues to flow and fill the bore 66, pilot valve chamber 74 and the main piston chamber 76. Simultaneously, gas flows from the duct 58 through the bleed hole 44 in the gas delivery tube 46 to fill the reservoir 48. From the reservoir 48 the gas flows through the gas passageways 120 to fill the annular chamber 84. After a sufficient interval, all chambers, spaces and flow channels are at a pressure P1.

The spacer 50 is provided in the reservoir 48 to allow the volume of gas contained in the reservoir to be varied. This capability of varying volume enables the device to be used for subcutaneous (usually relatively smaller volumes) and intramuscular (relatively larger volumes) injection. The bleed hole 44 is positioned adjacent to the valve body 60 such that a wider spacer 50 may be provided without interfering with the bleed hole 44. The diameter of the bleed hole 44 is small in comparison to the flow areas of the duct 58, bore 66 and gas passageways 120.

With the device in the ready state, as described above and as illustrated in FIG. 3, the piston face 88 of the main valve piston 82 is sealed against the liner seat 94 of the liner 92, such that no gas may flow through the liner opening 104. The main valve piston 82 is forced against the liner seat 94 to make the seal by virtue of the pressure exerted on the back of the main valve piston, i.e. the surface facing the main piston chamber 76. Although in the ready state, the annular chamber 84 and in the main piston chamber 76 have equal gas pressure, the projected area of the main valve piston 82 facing the main piston chamber 76 is greater than the projected area of the main valve piston 82 facing the annular chamber 84. The resulting force imbalance causes the main valve piston 82 to be tightly sealed against the liner seat 94.

Using known techniques, the desired injectant is loaded into the ampule 132. Single-use ampules may be provided as a unit along with the plunger 96 and the shield 160. Unit-dose ampules prefilled with injectant may also be used. These ampules have a relatively larger surface around the nozzle 148 and no Luer fitting. Correspondingly, the throat 140 of such ampules may be shortened. The base 146 of prefilled ampules is sealed with a plug or membrane.

With the ampule 132 loaded with injectant, the ampule holder 130 is placed over the ampule 132 and the threaded end 128 of the ampule holder 130 is engaged by the threaded collar 102. The plunger 96 passes through the threaded collar 102 and extends into the plunger driver 90 in the plunger chamber 114. (See FIG. 2.) The injection device is then ready for injection, by placing the device 20 against the patient's skin. (See FIG. 1).

As the front surface of the ampule 132 is relatively small, the shield 160 advantageously is provided over the Luer fitting 150 of the ampule 132 to help steady the injection device 20 against the patient's skin. The ridges 164 on the front surface 162 of the shield 160 help to prevent sliding over the patient's skin and local anesthetic phenomenon. The flange 166 of the shield 160 cover the ampule holder surface 30 and is intended to help to prevent bodily fluids from contacting the reusable ampule holder 130.

During the injection sequence, substantial pressure is developed within the injectant chamber 134. Consequently, it is advantageous to avoid overstressing the injectant chamber walls 136. The ampule holder 130 may help to prevent excessively stressing the Luer fitting 150, the transition 138 or the injectant chamber walls 136 of the ampule 132 by at least partially transferring stresses (which may be generated by lateral or bending movement of the nozzle 148 against the patient's skin) to the ampule holder 130.

With the device 20 in the ready state and held against the patient's skin, the device 20 is activated by depressing the button 70. This causes the pilot valve 72 to open permitting the compressed gas in the pilot valve chamber 74 to escape through vent 78 to the outside. Simultaneously, the gas in the main piston chamber 76 rushes outwardly along the same path causing a substantial pressure drop therein. The small diameter of the bleed hole 44 in the gas delivery tube 46 severely restricts the flow of gas from the annular chamber 84 through the gas passageways 120 and reservoir 48 in&:o the duct 58. Similarly, the orifice 42 severely restricts the flow of gas from the cartridge 28. As a result, at the instant just after the button 70 is depressed, the pressure in the annular chamber 84 is far higher than the pressure in the main piston chamber 76. The main valve piston 82 is thereby rapidly driven in a snap action backwards towards the pilot valve chamber 74 such that the seal between the piston face 88 and the liner 94 is opened, as shown in phantom in FIG. 3. The gas in the reservoir 48 is then able to flow through the gas passageways 120 and through the opening 104 into the plunger chamber 114 to drive the plunger driver 90 and plunger 96 into the injectant chamber 13 of the ampule 132. As the plunger 96 and plunger driver 90 move outwardly toward the ampule 130, the plunger chamber 114 is vented through the plunger chamber vent 122. The rapid acceleration of the plunger 96 causes the injectant to be injected out of the nozzle 148 at a pressure and velocity sufficient to pass through the patient's skin.

During the injection sequence, a small amount of compressed "bleed" gas may also flow from the cartridge 28 and reservoir 48 into the pilot valve chamber and out through the vent 78. However, this quantity of gas is acceptably small in comparison to the "driving" gas flowing from the reservoir 48 into the plunger chamber 114. In addition, since the volume of the reservoir 48 is large compared to the initial "dead" volume between plunger driver 90 and the main valve, the rise in gas pressure acting on the plunger driver 90 is very fast.

Following the injection, the button 70 is released and the pilot valve 72 closes. The gas pressures in the various ducts and chambers within the housing 22 then once again equalize and return substantially to P1. Specifically, compressed gas from the cartridge 28 flows through the bleed hole 44 to repressurize the reservoir 48 and through the duct 58 to repressurize the bore 66, pilot valve chamber 74 and main piston chamber 76. Due to the small size of the openings in the orifice 42 and the bleed hole 44, this repressurization occurs slowly in comparison to the injection sequence. As the main piston chamber 76 is repressurized, the main valve piston 82 is driven forward so that the piston face 88 once again seals against the liner seat 94. In the plunger chamber 114, the spring 116 pushes the plunger driver 90 back against the opening 104. As the plunger driver 90 is returned to its original ready position, remaining gas in the plunger chamber 114 vents through the plunger driver orifice 112.

To prepare the device 20 for the next injection, the ampule holder 130, the ampule 132 and the plunger 96 are removed from the housing 22 by unscrewing the ampule holder 130 from the threaded collar 102. A new ampule assembly 100 is then filled with injectant and installed on the device 20 as previously described.

Depending upon the particular application, the gas cartridge 28 is sufficient for several injections. To replace the cartridge 28 after a predetermined number of injections, the cartridge holder 24 is unscrewed from the housing 22. As the cartridge holder 24 is being unscrewed from the housing 22, remaining compressed gas in the cartridge 28 may escape from the cartridge 28 into the interior of the cartridge holder 24. The opening 26 at the end of the cartridge holder 24 prevents the cartridge holder 24 from becoming pressurized, such that the cartridge holder 24 may be easily removed from the housing 22. A new gas cartridge 28 is then installed as previously described.

The device 20 may be used for intramuscular or subcutaneous injections. For subcutaneous injection, the nozzle 148 has a relatively smaller opening and the reservoir 48 is largely occupied by a spacer 50, limiting the gas volume therein to preferably as little as 20% of the full reservoir volume. For intramuscular injection, a larger nozzle 148 opening is advantageously used and the reservoir may be up to 100% filled with "driving" gas, i.e., no spacer is used. The nozzle 148 opening may range in diameter 0 from approximately 0.004 to 0.025 inches. The nozzle diameter and spacer 50 size (or length) determine whether the device is set up for intramuscular or subcutaneous injection.

Various other design alternatives will be apparent to those skilled in the art. For example, the various O-rings which seal non-moving components within the housing 22 may be replaced or eliminated by other types of seals (including adhesives) or internal construction. In addition, a diaphragm or bellows could be used in place of the main valve piston 82 and various other configurations of the valves, chambers and flow passageways are also possible.

Thus, while several embodiments of the present invention have been shown and described, it will be obvious that many changes and modifications may be made thereunto, without departing from the spirit and scope of the invention.

What is claimed is:

1. An injection device comprising:
a housing;
a plunger driver slidably disposed within said housing;
a pilot valve within said housing connectable to a compressed gas source; and
a main valve having a substantially unbiased main valve piston, said main valve operatively connected to said pilot valve, said pilot valve activatable to open said main valve such that compressed gas may flow by said main valve to drive said plunger driver.

2. The injection device of claim 1 further comprising: a cartridge holder attachable to said housing and having a cartridge chamber;
a valve body disposed within said housing; and
a gas delivery tube connecting said cartridge chamber and said valve body.

3. The injection device of claim 2 further comprising a piercing body spaced apart from said valve body and forming a reservoir therebetween.

4. The injection device of claim 2 further comprising a gas filter associated with said gas delivery tube.

5. The injection device of claim 2 further comprising at least one bleed hole in said gas delivery tube.

6. The injection device of claim 1 further comprising a liner having a liner seat, and a main valve piston with said main valve piston and said liner seat comprising said main valve.

7. The injection device of claim 3 wherein at least said liner and said main valve piston form an annular chamber between said liner and said main valve piston with said annular chamber connected by at least one gas passageway to said reservoir.

8. The injection device of claim 7 wherein said gas passageway comprises a slot on said valve body.

9. The injection device of claim 6 wherein said main valve piston has a sealing face including an elastomeric seal.

10. The injection device of claim 1 wherein said pilot valve comprises a Schrader-type poppet valve.

11. An injection device comprising:
a housing;
a plunger driver within said housing;
a valve body within said housing;
a pilot valve within a pilot valve chamber in said valve body;
a main valve having a main valve seat within said housing and a substantially unbiased main valve piston sealingly engageable to said main valve seat;
a gas delivery tube connectable to a compressed gas source and joined to said pilot valve chamber and said main piston chamber, said gas delivery tube having a bleed hole leading to a reservoir;
said pilot valve activatable to create a gas pressure difference on opposite sides of said main valve causing it to separate from said valve seat such that compressed gas in said reservoir is released to drive said plunger driver.

12. An injection device comprising:
a housing;
a plunger driver slidably positioned within said housing;
a piercing body within said housing;
a valve body in said housing spaced apart from said piercing body;
a gas delivery tube extending from said piercing body to said valve body;
a reservoir formed at least by said valve body and said housing, said gas delivery tube having a bleed hole opening to said reservoir;
a pilot valve substantially disposed in a pilot valve chamber in said valve body;
a main valve seat;
a main valve piston slidably disposed within said housing and sealingly engageable against said main valve seat;
said main valve piston having a first chamber on a first side thereof, said first chamber connected to said reservoir via a gas passageway, said main valve piston having a second chamber on a second side thereof, said second chamber connecting to said pilot valve chamber;
said pilot valve activatable to vent said pilot valve chamber thereby causing said main valve piston separate from said main valve seat such that compressed gas from said reservoir flows past said main valve piston into a plunger chamber to drive said plunger driver.

13. The injection device of claim 12 further comprising a sleeve section on said valve body with said main valve piston slidably displaceable within said sleeve section.

14. An injection method comprising the steps of:

positioning a nozzle of an injection device onto an injection site;

activating a biased pilot valve of the device; and allowing an unbiased main valve of the device to open in response to activation of the pilot valve, thereby allowing compressed gas to pass by the main valve to drive injectant from the nozzle.

15. The method of claim 14 further comprising the step of supplying compressed gas to the pilot valve.

16. The method of claim 15 further comprising the step of supplying compressed gas from the reservoir around the pilot valve to the main valve via a gas passageway.

17. The method of claim 14 further comprising the step of supplying compressed gas to a reservoir.

18. The method of claim 14 wherein compressed gas is supplied to the pilot valve by connecting a compressed gas cartridge to a gas delivery tube leading to the pilot valve.

19. The method of claim 18 further comprising the step of bleeding gas from the gas delivery tube to the reservoir.

20. The method of claim 14 further comprising the step of metering the compressed gas supplied to the pilot valve by passing it through an orifice.

21. The method of claim 14 wherein said nozzle is on an ampule releasably attached to the injection device, further comprising the step of using the compressed gas flowing by the main valve to drive a plunger into the ampule.

22. A method of intramuscular and subcutaneous injection comprising the steps of:

installing an ampule containing an injectant and having a nozzle into a holder on an injector;

placing the nozzle of the ampule onto an injection site;

activating a biased pilot valve to vent a pilot valve chamber;

opening an unbiased main valve with a gas pressure difference across opposite sides of the main valve resulting from activation of the pilot valve; and driving a plunger into the ampule with gas pressure developed by compressed gas flowing past the main valve to drive the injectant out of the ampule through the nozzle.

23. The method of claim 22 further comprising the step of connecting a compressed gas source to the pilot valve chamber, a reservoir and a seat chamber.

24. An injection device assembly comprising:

a device housing;

a pilot valve within said device housing connectable to a compressed gas source;

an ampule for holding an injectant, said ampule having a nozzle, and said ampule attachable to said device housing;

an unbiased main valve operatively connected to said pilot valve, said pilot valve activatable to open said main valve such that compressed gas may flow by said main valve to drive an injectant from said nozzle.

25. An injection device comprising:

a housing;

a plunger driver slidably disposed within said housing;

a pilot valve within said housing connectable to a compressed gas source;

a main valve operatively connected to said pilot valve, said pilot valve activatable to open said main valve such that compressed gas may flow by said main valve to drive said plunger driver;

a cartridge holder attachable to said housing and having a cartridge chamber;

a valve body disposed within said housing;

a gas delivery tube connecting said cartridge chamber and said valve body;

a piercing body spaced apart from said valve body and forming a reservoir therebetween; and a spacer disposed within said reservoir to limit the volume of said reservoir.

26. An injection device comprising:

a housing;

a plunger driver slidably disposed within said housing;

a pilot valve within said housing connectable to a compressed gas source;

a liner having a liner sheet;

a main valve piston having a central counterbore, said main valve piston and said liner seat comprising a main valve;

said main valve operatively connected to said pilot valve, and said pilot valve activatable to open said main valve such that compressed gas may flow by said main valve to drive said plunger driver.

27. An injection method comprising the steps of:

positioning a nozzle of an injection device onto an injection site;

activating a pilot valve of the device;

allowing a main valve of the device to open in response to activation of the pilot valve, thereby allowing compressed gas to pass by the main valve to drive injectant from the nozzle;

supplying compressed gas to a reservoir; and adjusting the volume of the reservoir.

28. An injection method comprising the steps of:

connecting a compressed gas cartridge to a gas delivery tube leading to the pilot valve, to supply compressed gas to a pilot valve within an injection device;

filtering the compressed gas supplied to the delivery tube;

positioning a nozzle of the injection device onto an injection site;

activating a pilot valve of the device;

allowing a main valve of the device to open in response to activation of the pilot valve, thereby allowing compressed gas to pass by the main valve to drive injectant from the nozzle;

29. A method of intramuscular and subcutaneous injection comprising the steps of:

installing an ampule containing an injectant and having a nozzle into a holder on an injector;

placing the nozzle of the ampule onto an injection site;

activating a pilot valve to vent a pilot valve chamber;

opening a main valve with a gas pressure difference across opposite sides of the main valve resulting from activation of the pilot valve;

driving a plunger into the ampule with gas pressure developed by compressed gas flowing past the main valve to drive the injectant out of the ampule through the nozzle;

releasing the pilot valve and resealing the pilot valve chamber;

refilling the pilot valve chamber with compressed gas; and closing the main valve.

30. A method of intramuscular and subcutaneous injection comprising the steps of:
- installing an ampule containing an injectant and having a nozzle into a holder on an injector;
- connecting a compressed gas source to a pilot valve chamber, a reservoir and a seat chamber within the injector;
- placing the nozzle of the ampule onto an injection site;
- activating a pilot valve to vent a pilot valve chamber;
- opening a main valve with a gas pressure difference across opposite sides of the main valve, resulting from activation of the pilot valve;
- driving a plunger into the ampule with gas pressure developed by compressed gas flowing past the main valve, to drive the injectant out of the ampule through the nozzle;
- selecting an ampule opening and a spacer for the reservoir for one of intramuscular and subcutaneous injection.

* * * * *

UNITED STATES PATENT AND TRADEMARK OFFICE
CERTIFICATE OF CORRECTION

PATENT NO. : 5,064,413

DATED : November 12, 1991

INVENTOR(S) : Charles M. McKinnon, et al.

It is certified that error appears in the above-identified patent and that said Letters Patent is hereby corrected as shown below:

Abstract, line 7, delete "driven" and insert -- drive --.

Column 3, line 67, delete "1!8" and insert -- 118 --.

Column 4, line 26, delete "!40" and insert -- 140 --.

Column 4, line 57, delete "3" and insert -- 38 --.

Column 5, line 67, delete "!36" and insert -- 136 --.

Column 6, line 13, delete "in&uo" and insert -- into --.

Column 6, line 26, delete "13" and insert -- 134 --.

Column 7, line 23, after the word diameter delete "0".

Signed and Sealed this

Thirteenth Day of July, 1993

Attest:

MICHAEL K. KIRK

*Attesting Officer*  *Acting Commissioner of Patents and Trademarks*